(12) United States Patent
Angeletakis

(10) Patent No.: US 11,154,463 B2
(45) Date of Patent: Oct. 26, 2021

(54) LIGHT CURED ADDITION SILICONE IMPRESSION MATERIAL WITH IMPROVED STORAGE STABILITY

(71) Applicant: DENTSPLY SIRONA Inc., York, PA (US)

(72) Inventor: Christos Angeletakis, Bear, DE (US)

(73) Assignee: DENTSPLY SIRONA INC., York, PA (US)

( * ) Notice: Subject to any disclaimer, the term of this patent is extended or adjusted under 35 U.S.C. 154(b) by 111 days.

(21) Appl. No.: 16/369,440

(22) Filed: Mar. 29, 2019

(65) Prior Publication Data

US 2019/0298622 A1  Oct. 3, 2019

Related U.S. Application Data

(60) Provisional application No. 62/650,439, filed on Mar. 30, 2018.

(51) Int. Cl.

| | | |
|---|---|---|
| *A61K 6/90* | (2020.01) | |
| *C08L 83/04* | (2006.01) | |
| *A61K 6/71* | (2020.01) | |
| *A61K 6/77* | (2020.01) | |
| *A61K 6/822* | (2020.01) | |
| *C08G 77/12* | (2006.01) | |
| *C08G 77/20* | (2006.01) | |
| *C08K 5/00* | (2006.01) | |
| *C08K 9/08* | (2006.01) | |

(52) U.S. Cl.
CPC ............... *A61K 6/90* (2020.01); *A61K 6/71* (2020.01); *A61K 6/77* (2020.01); *A61K 6/822* (2020.01); *C08L 83/04* (2013.01); *C08G 77/12* (2013.01); *C08G 77/20* (2013.01); *C08K 5/0025* (2013.01); *C08K 9/08* (2013.01); *C08K 2201/005* (2013.01)

(58) Field of Classification Search
CPC ........................................................ A61K 6/90
See application file for complete search history.

(56) References Cited

U.S. PATENT DOCUMENTS

| 4,077,937 | A | | 3/1978 | Sato | |
| 5,145,886 | A | | 9/1992 | Oxman | |
| 5,583,178 | A | * | 12/1996 | Oxman | ................ C09B 23/145 524/862 |
| 6,313,190 | B1 | | 11/2001 | Bublewitz | |
| 9,193,849 | B2 | | 11/2015 | Stelzig | |
| 2007/0060717 | A1 | * | 3/2007 | Zech | ...................... C08L 83/04 525/478 |
| 2008/0033071 | A1 | | 2/2008 | Irmer | |
| 2014/0004359 | A1 | | 1/2014 | Marrot | |

FOREIGN PATENT DOCUMENTS

| EP | 1361253 A1 | 11/2003 |
| EP | 3058932 A1 | 8/2016 |

OTHER PUBLICATIONS

International Search Report; PCT/US2019/024806; Jul. 12, 2019 (completed); dated Jul. 23, 2019 (mailed).
International Preliminary Report on Patentability; PCT/US2019/024806; Jul. 12, 2019 (completed); dated Jul. 23, 2019 (mailed).
Written Opinion of the International Searching Authority; PCT/US2019/024806; Jul. 12, 2019 (completed); dated Jul. 23, 2019 (mailed).
Interaction Between Pt(acac)2 and Alumina Surfaces Studied by XAS; Womes, M., Lynch, J., Bazin, D. et al.: Catalysis Letters, 2003, 25-31,85.
Preparation and characterization of supported mononuclear metal complexes as model catalysts; Jeffrey C. Kenvin, Mark G. White, and Mark B. Mitchell: Langmuir 1991,1198-1205,7, 6, Publication Date:Jun. 1, 1991.

* cited by examiner

*Primary Examiner* — Robert T Butcher
(74) *Attorney, Agent, or Firm* — Dentsply Sirona Inc.

(57) ABSTRACT

The present disclosure generally relates to a curable one part silicone composition. The curable one part silicone composition includes an organopolysiloxane compound having at least two unsaturated groups; an organohydrogenpolysiloxane compound having at least two Si—H groups; a catalyst for enabling the addition of the hydrogen atoms bonded to the silicone to the unsaturated group; and at least one surface treated particulate filler. The curable one part silicone composition is useful as a dental impression material. More particularly, the curable one part silicone composition including the surface treated filler extends storage stability of the dental impression material. The disclosure also provides methods of preparing such curable one part silicone composition.

16 Claims, No Drawings

LIGHT CURED ADDITION SILICONE IMPRESSION MATERIAL WITH IMPROVED STORAGE STABILITY

FIELD OF THE DISCLOSURE

The present disclosure generally relates to a curable one part silicone composition. The curable one part silicone composition includes an organopolysiloxane compound having at least two unsaturated groups; an organohydrogenpolysiloxane compound having at least two Si—H groups; a catalyst for enabling the addition of the hydrogen atoms bonded to the silicone of the organohydrogenpolysiloxane compound to the unsaturated group of the organopolysiloxane compound; and at least one surface treated particulate filler. The curable one part silicone composition is useful for preparation of dental impression material, soft relining material for dentures, template material for provisional crown and bridge restorative. More particularly, the curable one part silicone composition including the surface treated filler extends storage stability of the dental impression material. The disclosure also provides methods of preparing such curable one part silicone composition.

BACKGROUND OF THE DISCLOSURE

In dentistry, addition silicones are the most widely used impression materials. Addition curing silicones are widely used as impression materials in dentistry for their high accuracy and dimensional stability. These are usually of the two-part type cured via a hydrosilation reaction, passed through a mixing tip and are set within a few minutes in the mouth to give accurate impressions. These also contain silica fillers to provide reinforcement and increase hardness. Commonly used catalyst for this reaction is Karstedt's Catalyst, a complex of Platinum (0) with Divinyltetramethyldisiloxane (DVTMDS). However, it will be an advantageous to have a single component material cured on demand as it would shorten the overall time to take an impression.

Light curable silicones used in industrial applications usually are cured by a platinum-based catalyst that will not catalyze a hydrosilation reaction in the presence of hydride functional polydimethylsiloxanes (HPDMS) except by exposure to light. Common catalysts used for this application are platinum diacetoacetate ($Pt(acac)_2$) and Trimethyl (methylcyclopentadienyl)platinum ($(Me-Cp)Pt(Me)_3$). However, these catalysts are unstable in the presence of crosslinkers or HPDMS together with silica fillers. Pot life is of the order of a few hours to a few days. Therefore, these are premixed immediately to several hours before use. This instability is unacceptable for a dental impression material however where shelf life at room temperature is expected to be 1 year or longer.

Oxman and Boardman, U.S. Pat. No. 5,145,886 describes a dental impression LC silicone formulations which is mostly based on using Platinum (II) acetylacetonate {Pt $(acac)_2$} as catalyst. Stability of over 150 days is claimed without the use of an inhibitor although inhibitors such as acetylenic alcohols and phosphites are mentioned. In our hands, stability of a few hours was noted for one of the example formulations mentioned, more akin with light cured silicones currently marketed for industrial applications such as Uvisil by Wacker Corp. and similar materials by Momentive.

Irmer et al., US Patent Application Publication US 2008/0033071 describes two-part LC silicone formulations that optionally contains alkynols and vinyl siloxanes as inhibitors. These extend the pot life of the mix for a few hours for their intended use.

Marrot et al., US Patent Application Publication US2014/0004359 describes a two-part LC silicone system used as a film in paper release for packaging applications. It further discloses use of acetylenic diols together with acids to extend pot life after mixing to about 24 hours.

All the one part light curable silicones curable by a hydrosilation reaction use silica as the filler to obtain desirable strength and viscosity characteristics. However, it has been suggested, based on controlled studies that silica may catalyze the formation of Platinum zero species Pt (0) leading to degradation (J C Kenvin et al, Langmuir Vol. 7, 1198 (1991) and M. Womes et al, Catalysis Letters Vol. 85, pg. 25 (2003).

SUMMARY OF THE DISCLOSURE

As discussed above, there is a continuing need for a curable impression material formulation with good curing that contains a silica filler and is more stable. Also, it will be an advantageous to have a single component material cured on demand as it would shorten the overall time to take an impression.

It is an object of the present disclosure to provide a curable one part silicone composition for a dental impression material that is capable of extending the storage stability of the dental impression material. This is accomplished by including surface treated particulate filler into the composition. The surface treated particulate filler would render the surface silanol groups less reactive.

In a first aspect of the present disclosure disclosed is a curable one part silicone composition for a dental impression material. The silicone composition comprises (a) an organopolysiloxane compound having at least two unsaturated groups; (b) an organohydrogenpolysiloxane compound having at least two Si—H groups; (c) a catalyst for enabling the addition of the hydrogen atoms bonded the silicone of the organohydrogenpolysiloxane compound to the unsaturated group of the organopolysiloxane compound; and (d) at least one surface treated particulate filler.

According to one embodiment of the curable one part silicone composition, the surface treated filler extends storage stability of the dental impression material.

According to another embodiment of the curable one part silicone composition, the organopolysiloxane compound having at least two unsaturated groups includes vinyl terminated polydimethylsiloxane.

According to one embodiment of the curable one part silicone composition, the organohydrogenpolysiloxane compound having at least two Si—H groups is HPDMS.

According to another embodiment of the curable one part silicone composition, the catalyst is selected from the group consisting of $Pt(acac)_2$, Platinum(II) Bis(dibenzoylmethanate) and Platinum(II) Bis(benzoylacetonate), and (Me-Cp) $Pt(Me)_3$.

According to one embodiment of the curable one part silicone composition, the at least one surface treated particulate filler is selected from the group consisting of an inorganic particulate filler, a submicron silica or oxides, and an inorganic filler.

In one particular embodiment, the at least one surface treated particulate filler is calcium aluminosilicate filler coated with a crosslinked acrylic resin.

According to one embodiment of the curable one part silicone composition, the surface treated particulate filler is prepared by a process of preparation of composite filler particles. The process include the steps of:

(a) coating a particulate filler having a median particle size (D50) of from 100 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler in the presence of a further crosslinking agent and in the presence of a further particulate filler not displaying reactive groups, for providing a granulation of the coated particulate filler wherein the granulation contains the coated particulate filler particles and the further particulate filler particles separated from and connected to each other by at least one coating layer, whereby the at least one coating layer may be crosslinked by crosslinking groups obtained by reacting the reactive groups and the further crosslinking agent, whereby the agglomeration is carried out by spray agglomeration or growth agglomeration;

(c) milling, classifying and sieving the granulation of the coated particulate filler; and (d) further crosslinking the granulation of the coated particulate filler;

wherein the prepared filler particles have a median particle size (D50) of from 1 to 70 μm;

wherein reactive groups are transformed into crosslinking groups obtained by reacting reactive groups and a further crosslinking agent; and wherein the particulate filler is the main component by volume of the composite filler particles.

Other aspects will be set forth in the description which follows, and in part will be apparent from the description or may be learned from the practice of the present disclosure.

DETAILED DESCRIPTION OF THE DISCLOSURE

Disclosed herein is a curable one part silicone composition, method of using the curable one part silicone composition for preparation of dental impression material, soft relining material for dentures, template material for provisional crown and bridge restorative and method of preparing such curable one part silicone composition.

In a first aspect of the present disclosure there is provided a curable one part silicone composition for a dental impression material. The curable one part silicone composition comprise, in general: (a) an organopolysiloxane compound having at least two unsaturated groups; (b) an organohydrogenpolysiloxane compound having at least two Si—H groups; (c) a catalyst for enabling the addition of the hydrogen atoms to the silicone of the organohydrogenpolysiloxane compound to the unsaturated group of the organopolysiloxane compound; and (d) at least one surface treated particulate filler.

(a) An Organopolysiloxane Compound Having at Least Two Unsaturated Groups

The unsaturated group is selected from vinylic or acetylenic group.

In certain embodiments of the curable one part silicone composition disclosed herein; the organopolysiloxane compound having at least two unsaturated groups is selected from the group consisting of vinyl terminated polydimethylsiloxane, trifunctional siloxanes, quadrifunctional siloxanes, and organopolysiloxanes containing phenyl groups.

Examples of a trifunctional siloxane include trifunctional polydimethyl siloxane with vinyl group. The trifunctional polydimethyl siloxane with vinyl group is vinyl T-structure Polymer VTT-106 (Gelest).

Examples of a quadrifunctional siloxane include quadrifunctional siloxane with vinyl groups. The quadrifunctional siloxane with vinyl groups may be vinyl Q Resin Dispersion VQM-135 (Gelest) and Momentive H6 polymer (a mixture of QM resin and vinylpolysiloxane resin).

QM Resin dispersions have a viscosity of about 5,000-60,000 cps. These dispersions may comprise a plurality of dispersion components having desired viscosities and QM resin contents. The QM resin comprises about 20-25 weight % of each dispersion.

Examples of an organopolysiloxanes containing phenyl groups includes Vinyl Terminated Diphenylsiloxane-Dimethylsiloxane Copolymers. The vinyl terminated Diphenylsiloxane-Dimethylsiloxane Copolymers may be PDV-0325 and PDV-1631 (Gelest).

In one particular embodiment of the curable one part silicone composition disclosed herein, the organopolysiloxane compound having at least two unsaturated groups is vinyl terminated polydimethylsiloxane type (divinyl PDMS).

In certain embodiments of the curable one part silicone composition disclosed herein, the organopolysiloxane compound having at least two unsaturated groups is present in a concentration of from 10% to 90% by weight based on the total weight of the silicone composition. In embodiment, such as in the concentration range of from 20% to 80% by weight.

(b) An Organohydrogenpolysiloxane Compound Having at Least Two Si—H Groups

In certain embodiments of the curable one part silicone composition disclosed herein; the organohydrogenpolysiloxane compound having at least two Si—H groups is HPDMS.

In certain embodiments of the curable one part silicone composition disclosed herein, the hydride content in HPDMS is from about 3.5 mmol/g to about 4.9 mmol/g; In embodiments, the hydride content in HPDMS is 4.3 mmol/g.

In certain embodiments of the curable one part silicone composition disclosed herein, the organohydrogenpolysiloxane compound having at least two Si—H groups is present in a concentration of from 1% to 20% by weight based on the total weight of silicone composition; such as in concentration range of 3% to 10% by weight.

(c) A Catalyst

The catalyst which are useful for catalyzing the reaction of the hydrogen atom bonded to the silicone of the organohydrogenpolysiloxane compound to the unsaturated groups of the organopolysiloxane compound by exposure to light may be Platinum (II) or Platinum (IV) compounds.

Examples of Platinum (II) compounds may include but not limited to Pt(acac)$_2$, Platinum(II) Bis(dibenzoylmethanate) and Platinum(II) Bis(benzoylacetonate).

Example of Platinum (IV) compound includes (Me-Cp)Pt(Me)$_3$.

In certain embodiments of the curable one part silicone composition disclosed herein, the catalyst is selected from the group consisting of Pt (acac)$_2$, Platinum(II) Bis(dibenzoylmethanate) Platinum(II) Bis(benzoylacetonate), and (Me-Cp)Pt(Me)$_3$.

In a particular embodiment of the curable one part silicone composition disclosed herein, the catalyst is Pt (acac)$_2$.

In certain embodiments of the curable one part silicone composition disclosed herein, the catalyst is added in an amount of about 20 to 500 ppm based on total weight of silicone composition; such as in concentration range of 50 to 200 ppm.

(d) Surface Treated Particulate Filler

The particulate filler has a median particle size (D50) of 1 to 1200 nm, such as of from 10 to 1000, particularly of from 20 to 800 nm as measured using, for example, electron microscopy or by using a conventional laser diffraction particle sizing method as embodied by a MALVERN Mastersizer S or MALVERN Mastersizer 2000 apparatus.

According to a specific embodiment, the particulate filler has a median particle size (D50) of 100 to 800 nm.

The particulate filler is not particularly limited as long as the material of the particulate filler is acceptable for dental applications.

The curable one part silicone composition may include more than one surface treated particulate filler.

In certain embodiments of the curable one part silicone composition disclosed herein, the at least one surface treated particulate filler is selected from the group consisting of an inorganic particulate filler, a submicron silica or oxides and an inorganic filler.

The inorganic particulate includes but not limited to dental glasses, fused silica, quartz, crystalline silica, amorphous silica, soda glass beads, glass rods, ceramic oxides, particulate silicate glass, and radiopaque glasses.

It is also possible to employ finely divided materials and powdered hydroxyapatite, although materials that react with silane coupling agents are preferred.

In certain embodiments of the curable one part silicone composition disclosed herein, the submicron silica or oxide is selected from the group consisting of fumed silica, precipitated silica and aluminosilicates.

Examples of aluminosilicates include but not limited to calcium aluminosilicate, strontium aluminosilicate and barium aluminosilicates.

The inorganic filler is may be $YF_3$, $La_2O_3$, $ZrO_2$, $BiPO_4$, $CaWO_4$, $BaWO_4$, $SrF_2$, or $Bi_2O_3$.

The surface treated filler particles in general may be obtained by a process for the preparation of composite filler particles as disclosed in U.S. Pat. No. 9,193,849, the disclosure of which is herein incorporated by reference in its entirety.

In certain embodiments of the curable one part silicone composition disclosed herein, the surface treated particulate filler is prepared by a process of preparation of composite filler particles. The process includes the steps of:

(a) coating a particulate filler having a median particle size (D50) of from 100 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler in the presence of a further crosslinking agent and in the presence of a further particulate filler not displaying reactive groups, for providing a granulation of the coated particulate filler wherein the granulation contains the coated particulate filler particles and the further particulate filler particles separated from and connected to each other by at least one coating layer, whereby the at least one coating layer may be crosslinked by crosslinking groups obtained by reacting the reactive groups and the further crosslinking agent, whereby the agglomeration is carried out by spray agglomeration or growth agglomeration;

(c) milling, classifying and sieving the granulation of the coated particulate filler; and (d) further crosslinking the granulation of the coated particulate filler;

wherein the prepared filler particles have a median particle size (D50) of from 1 to 70 µm;

wherein reactive groups are transformed into crosslinking groups obtained by reacting reactive groups and a further crosslinking agent; and wherein the particulate filler is the main component by volume of the composite filler particles.

In one particular embodiment, the surface treated particulate filler is particulate calcium aluminosilicate filler coated with a crosslinked acrylic resin.

In certain embodiments of the curable one part silicone composition disclosed herein, the surface treated silica filler is present in a concentration of from 10% to 80% by weight based on the total weight of the composition; such as in concentration range of 15% to 60%.

In certain embodiments of the curable one part silicone composition disclosed herein, wherein the surface treated particulate filler have a median particle size of from 1 to 50 µm. Particle size of the surface treated particulate filler may be less than 74 µm. In embodiments, the particle size of the surface treated particulate filler is less than 40 µm.

According to one embodiment of the curable one part silicone composition, the surface treated filler extends storage stability of the dental impression material.

The surface treated particulate filler would render the surface silanol groups less reactive.

Preparation of Curable One Part Silicone Composition

In a second aspect of the present disclosure disclosed is a method of preparing a curable one part silicone composition. The curable one part silicone composition may be prepared by combining an organopolysiloxane compound having at least two unsaturated groups, organohydrogenpolysiloxane compound having at least two Si—H groups and a catalyst in essentially any order with stirring to form a activated silicon resin composition. The at least one surface treated particulate filler is then added to the activated silicon resin composition.

The curable one part silicone composition may be prepared by combining an organopolysiloxane compound having at least two unsaturated groups with an organohydrogenpolysiloxane compound having at least two Si—H groups initially, followed by addition of the catalyst to form a activated silicon resin composition and then adding at least one surface treated particulate filler to the activated silicon resin composition.

Use and Curing of Curable One Part Silicone Composition

The curable one part silicone composition can be used to form a cured material. Cure generally can be affected at temperature ranging from 20 to 23° C. The curable one part silicone composition of the present disclosure may be cured by LED dental curing light with a special head that emits light from 350 nm to 700 nm. In particular, the LED dental curing light emits light at 405 nm.

The cured material is dental impression material, soft relining material for dentures, template material for provisional crown and bridge restorative.

In one particular embodiment, the cured material is an impression material. More particularly, a light cured silicone paste.

The disclosure discussed herein is further illustrated by the compositions described in the following Examples, but these Examples should not be construed as limiting the scope of the present disclosure.

Experimental

Test Methods

Curing was accomplished using a LED dental curing light (Fusion Lite) with a special head that emits at 405 nm.

Stability was tested by placing the paste in 50° C. forced air oven or allowed to stand in temperature-controlled room where the variation was 22-27° C. Polymerization was assessed by poking with a plastic stick. When material was not easily penetrated was judged as polymerized.

Consistency was performed according to IS04823 guidelines. A 500 g weight was used for 30 seconds and then the diameter was measured.

Strain in compression was performed according to IS4823. A 20 seconds light exposure on each side on a 8 mm by 10 mm specimen was used.

Shore A Hardness: Test was performed according to DIN 53505. Mold size was 8 mm in diameter and 10 mm deep. Light exposure was 20 seconds on one side only.

Depth of Cure: Test was performed according to ISO 4049 guidelines.

Opacity: Test was performed according to ISO 4049 guidelines

Example Formulation

A formulation example is described in Table 1. The Activated Silicon Resin composition is shown in Table 1. For the preparation of Activated Silicon Resin, a platinum catalyst, Pt(acac)$_2$, was added to give a final concentration of 0.01% or 100 ppm. Paste formulations are shown in Table 2 and contain the following types of surface treated particulate fillers: Sipernat D13 (Evonik) is a hydrophobic precipitated silica; Aerosil R972 (Evonik) is a hydrophobic fumed silica; A 1.5 µm sized surface treated particulate Calcium Aluminosilicate filler coated with a crosslinked acrylic resin prepared according to procedure of Example 10 described in U.S. Pat. No. 9,193,849 and EP2790639 (SphereTec process), the disclosure of which is herein incorporated by reference in its entirety.

Table 3 summarizes the stability studies.

TABLE 1

Activated Resin Composition.

| Activated Resin Composition | Parts |
| --- | --- |
| PDMS Hydride | 7.00 |
| 200 csk divinyl PDMS | 10.00 |
| 1000 csk divinyl PDMS | 58.99 |
| 10000 csk divinyl PDMS | 24.00 |
| Pt(acac)$_2$ | 0.01 |
| Total | 100.00 |

TABLE 2

Testing of Light Cured Silicone Pastes.

| | | | |
| --- | --- | --- | --- |
| Activated Resin | 80 | 80 | 75 |
| Sipernat D13 Precipitated Silica | 20 | 0 | 5 |
| Aerosil R972 fumed silica | 0 | 20 | 0 |
| Coated Calcium Aluminosilicate filler | 0 | 0 | 20 |
| Consistency mm | 43 | 43 | 43 |
| % Opacity | 25.7 | 33.7 | 74.5 |
| Shore A Hardness Top/Bottom at 3 minutes | 46/42 | 53/53 | 42/41 |
| Shore A Hardness Top/Bottom at 15 minutes | 53/51 | nd | nd |
| Strain in Compression % | 93.5 | 92.5 | 93 |
| Depth of Cure (20 seconds light exposure), mm | 11.4 | 15.1 | 7.6 |

TABLE 3

Stability of Light Curable Silicone Pastes.

| | | | | |
| --- | --- | --- | --- | --- |
| Activated Resin | 80 | 75 | 80 | 80 |
| Sipernat D13 | 0 | 5 | 20 | 0 |
| Aerosil R972 | 0 | 0 | 0 | 20 |
| Coated Calcium Aluminosilicate filler | 20* | 20 | 0 | 0 |
| Stability at 50° C. (days) | 20 | 14 | 6 | 2 |
| Stability at Room temperature (days) | 210 | 125 | 90 | 40 |

*Paste is separated at 1 day. Filler precipitated to the bottom.

From these results it can be seen that in a one-part addition silicone impression formulation, use of a coated filler described in this disclosure, namely a particulate Calcium Aluminosilicate filler coated with a crosslinked acrylic resin prepared by the process described in U.S. Pat. No. 9,193,849 give extended stability.

Workers skilled in the art will appreciate that various modifications can be made to the illustrated embodiments and description herein without departing from the spirit and scope of the present disclosure. Other embodiments of the invention are discussed throughout this application. Any embodiment discussed with respect to one aspect applies to other embodiments as well and vice versa. Each embodiment described herein and any obvious variation thereof is understood to be applicable to all embodiments of the invention. Given the description herein, combined with the knowledge of one of ordinary skill in the art to which the invention pertains, any embodiment described herein can be easily accomplished and/or further implemented with respect to any use, method, compound, composition, obvious variant thereof, or any combination thereof. It is intended that all such modifications within the spirit and scope of the present disclosure be covered by the appended claims.

The invention claimed is:

1. A curable one part silicone composition for a dental impression material comprising:
    (a) an organopolysiloxane compound having at least two unsaturated groups;
    (b) an organohydrogenpolysiloxane compound having at least two Si—H groups;
    (c) a catalyst for enabling the addition of the hydrogen atoms bonded to the silicone of the organohydrogenpolysiloxane compound to the unsaturated group of the organopolysiloxane compound; and
(d) coated calcium aluminosilicate filler;
wherein the one part silicone composition has stability at storage for at least 125 days at a temperature of from 22° C. to 27° C.

2. The curable one part silicone composition according to claim 1, wherein the organopolysiloxane compound having at least two unsaturated groups is selected from the group consisting of vinyl terminated polydimethylsiloxane, trifunctional siloxanes, quadrifunctional siloxanes, and organopolysiloxanes containing phenyl groups.

3. The curable one part silicone composition according to claim 2, wherein the organopolysiloxane compound having at least two unsaturated groups includes vinyl terminated polydimethylsiloxane.

4. The curable one part silicone composition according to claim 1, wherein the organohydrogenpolysiloxane compound having at least two Si—H groups is hydride functional polydimethylsiloxanes (HPDMS).

5. The curable one part silicone composition according to claim 4, wherein a hydride content in HPDMS is from about 3.5 mmol/g to about 4.9 mmol/g.

6. The curable one part silicone composition according to claim 1, wherein the catalyst is selected from the group consisting of Pt (acac)$_2$, Platinum(II) Bis(dibenzoylmethanate) and Platinum(II) Bis(benzoylacetonate), and (Me-Cp) Pt(Me)$_3$.

7. The curable one part silicone composition according to claim 6, wherein the catalyst is Pt (acac)$_2$.

8. The curable one part silicone composition according to claim 1, wherein the organopolysiloxane compound having at least two unsaturated groups is present in a concentration of from 10% to 90% by weight based on a total weight of the silicone composition.

9. The curable one part silicone composition according to claim 1, wherein the organohydrogenpolysiloxane compound having at least two Si—H groups is present in a concentration of from 1% to 20% by weight based on a total weight of silicone composition.

10. The curable one part silicone composition according to claim 1, wherein the catalyst is added in an amount of about 20 to 500 ppm based on a total weight of silicone composition.

11. The curable one part silicone composition according to claim 1, wherein the coated calcium aluminosilicate filler is present in a concentration of from 10% to 80% by weight based on a total weight of the composition.

12. The one part silicone composition according to claim 1, wherein the coated calcium aluminosilicate filler have a median particle size of from 1 to 50 μm.

13. The one part silicone composition according to claim 1, wherein the coated calcium aluminosilicate filler is calcium aluminosilicate filler coated with a crosslinked acrylic resin.

14. A method of preparing a curable one part silicone composition, said method comprising steps of:
(a) mixing an organopolysiloxane compound having at least two unsaturated groups with an organohydrogenpolysiloxane compound having at least two Si—H groups and a catalyst to form a activated silicon resin composition;
(b) adding coated calcium aluminosilicate filler to the activated silicon resin composition.

15. A cured dental material obtained by curing a composition comprising:
(a) an organopolysiloxane compound having at least two unsaturated groups;
(b) an organohydrogenpolysiloxane compound having at least two Si—H groups;
(c) a catalyst for enabling the addition of the hydrogen atoms bonded to the silicone of the organohydrogenpolysiloxane compound to the unsaturated group of the organopolysiloxane compound; and
(d) coated calcium aluminosilicate filler;
wherein the composition has stability at storage for at least 125 days at a temperature of from 22° C. to 27° C.

16. The cured dental material according to claim 15, wherein the dental material is dental impression material, soft relining material for dentures, template material for provisional crown and bridge restorative.

* * * * *